United States Patent [19]
Cochrum et al.

[11] Patent Number: 5,876,742
[45] Date of Patent: Mar. 2, 1999

[54] BIOLOGICAL TISSUE TRANSPLANT COATED WITH STABILIZED MULTILAYER ALGINATE COATING SUITABLE FOR TRANSPLANTATION AND METHOD OF PREPARATION THEREOF

[75] Inventors: Kent C. Cochrum, Davis; Susan A. Jemtrud, San Francisco, both of Calif.

[73] Assignee: The Regents of the University of California, Oakland, Calif.

[21] Appl. No.: 757,025

[22] Filed: Nov. 26, 1996

Related U.S. Application Data

[63] Continuation-in-part of Ser. No. 186,327, Jan. 24, 1994, Pat. No. 5,578,314.
[51] Int. Cl.$^6$ .............................. A61F 2/02; A01N 1/02; C12N 5/08
[52] U.S. Cl. .................. 424/424; 264/4.1; 435/182; 435/240.22; 435/240.241; 435/240.243; 623/11
[58] Field of Search .............................. 424/424; 264/4.1; 435/1.1, 177, 178, 179, 180, 182, 240.22, 240.241, 240.243; 623/11

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,663,286 | 5/1987 | Tsang et al. | 435/178 |
| 4,673,566 | 6/1987 | Goosen et al. | 424/19 |
| 4,689,293 | 8/1987 | Goosen et al. | 435/1 |
| 4,696,286 | 9/1987 | Cochrum | 128/1 |
| 4,744,933 | 5/1988 | Rha et al. | 264/4.3 |
| 4,749,620 | 6/1988 | Rha et al. | 428/402.2 |
| 4,789,550 | 12/1988 | Hommel et al. | 424/493 |
| 4,806,355 | 2/1989 | Goosen et al. | 424/424 |
| 5,175,093 | 12/1992 | Seifert | 435/41 |
| 5,227,298 | 7/1993 | Weber et al. | 435/178 |
| 5,334,640 | 8/1994 | Desai et al. | 524/56 |

FOREIGN PATENT DOCUMENTS

| | | |
|---|---|---|
| 2034633 | 1/1991 | Canada . |
| 2034641 | 1/1991 | Canada . |
| WO 9107951 | 6/1991 | WIPO . |
| WO 9324112 | 12/1993 | WIPO . |

OTHER PUBLICATIONS

Haug, Arne, Fractionation of Alginic Acid, Acta Chem. Scand. 13, No. 3 pp. 601–603, (195).

Chang, Thomas, M.S., Semipermeable Microcapsules, Science, vol. 146, pp. 524–525, (1964).

Haug, Arne, et al., Fractionation of Alginates by Precipitation with Calcium and Magnesium Ions, Acta Chem. Scand., No. 5, pp. 1221–1226, (1965).

Mosbach, Klaus, Entrapment of Enzymes and Microorganisms in Synthetic Cross–linked Polymers and their Application in Column Techniques, Acta Chem. Scan., No. 10, pp. 2807–2810, (1966).

Chang, Thomas, M.S., et al., Semipermeable Aqueous Microcapsules, Canadian Journal of Physiology and Parmacology, vol. 44, pp. 115–128, (1966).

Haug, Arne, et al., Studies on the Sequences of Uronic Acid Residues in Alginic Acid, Acta Chem. Scand. 21, No. 3, pp. 691–704, (1967).

(List continued on next page.)

*Primary Examiner*—Carlos Azpuru
*Attorney, Agent, or Firm*—Hana Verny

[57] ABSTRACT

A biological tissue transplant coated with a stabilized multilayer alginate coating and a method for preparation of the stabilized multilayer coating. Coating has three primary layers of the alginate with a polyamino acid barrier emplaced between a primary and a secondary layer. The secondary "halo" layer of soft gel is formed by a gel gradient created between weakly bound cross-linking gelling divalent cations of an alginate used for the primary layer of the coating and non-gelling counter ions of a non-ionic alginate of the secondary layer of the coating.

19 Claims, 5 Drawing Sheets

OTHER PUBLICATIONS

Smidsrod, Olav, et al., Dependence upon Uronic Acid Composition of Some–Ion–Exhange Properties of Alginates, Acta chem. Scand. 22, No. 6, pp. 1989–1997, (1968).

Kierstan, M. et al., The Immobilization of Microbial Cells, Subcellular Organelles, and Enzymes in Calcium Alginate gels, Biotechnology and Bioengineering, vol. XIX, pp. 387–397, (1977).

Klomp, G.F., et al., Hydrogels for Encapsulation of Pancreatic Islet Cells, Trans. Am. Soc. Artif. Intern. Organs, vol. XXV, pp. 74–76, (1979).

Plunkett, Marian, L., et al., Methods in Laboratory Investigation, Laboratory Investigation, vol. 62, No. 4, pp. 510–517, (1990).

Lim, Franklin, Microencapsulated Islets as Bioartificial Endocrine Pancreas, Science, vol. 210, pp. 908–910, (Nov. 1980).

Lim, Franklin, Microencapsulation of Living Cells and Tissues, Journal of Pharmaceutical Sciences, vol. 70, No. 4, pp. 351–354, (Apr. 1981).

Nilsson, Kjell, et al., A General Method for the Immobilization of Cells with Preserve Viability, European Journal of Applied Microbiology and Biotechnology, 17:319–325, (1983).

Gin, H., et al., Agarose encapsulation of islets of Langerhans: reduced toxicity in vitro, J. Microencapsulation, vol. 4, No. 3, pp. 239–242, (1987).

Nigam, Somesh, C., Techniques for Preparing Hydrogel Membrane Capsules, Biotechnology Techniques, vol. 2, No. 4 pp. 271–276, (1988).

Martinsen, A., Alginate as Immobilization Material: I. Correlation between Chemical and Physical Properties of Alginate Gel Beads, Biotechnology and Bioengineering, vol. 33, pp. 79–89, (1989).

Skjak–Braek, Gudmund, et al., Alginate as Immobilization Material. II: Determination of Polyphenol Contaminants by Fluorescence Spectroscopy, and Evaluation of Methods for Their Removal, Biotechnology and Bioengineering, vol. 33, pp. 90–94, (1989).

Darguy, S., et al., Comparative Study of Microencapsulated Rat Islets Implanted in Different Diabetic Models in Mice, Hormone. Met. Res. Suppl., 26:209–213, (1990).

Fritschy, Wilbert, M., Effect of Alginate Microencapsulation In Vitro Insulin Release from Rat Pancreatic Islets, Diabetes, vol. 40, pp. 37–43, (Jan. 1991).

Otterlei, Marit, et al., Induction of Cytokine Production from Human Monocyte Stimulated with Alginate, Journal of Immunotherapy, 10:286–291, (1991).

Soon–Shiong, P., An Immunologic Basis for the Fibrotic reaction to Implanted Microcapsules, Transplantaion Proceedings, vol. 23, No. 1, pp. 758–759, (Feb. 1991).

Lum, Zhao–Ping, et al., Prolonged Reversal of Diabetic State in NOD Mice by Xenografts of Microencapsulated Rat Islets, Diabetes, vol. 4, pp. 1551–1516, (Nov. 1991).

Goosen, Mattheus, F.A., et al., Fundamentals of Animal Cell Encapsulation and Immobilization, CRC Press, (1993).

Fujihara, Michio, et al., An influence of the structure of alginate on the chemotactic activity of macrophages and the antitumor activity, Carbohydrate Research, 243, pp. 211–216, (1993).

Haug, Arne, Composition and Properties of Alginates, Norwegian Institute of Seaweed Research, Report No. 30, (1964).

Smidsrod, Olav, Some Physical Properties of Alginates in Solution and in the Gel State, Norwegian Institute of Seaweed Research, Report No. 34, (1973).

BIOLOGICAL TISSUE TRANSPLANT COATED WITH STABILIZED MULTILAYER ALGINATE COATING SUITABLE FOR TRANSPLANTATION AND METHOD OF PREPARATION THEREOF

This application is a continuation-in-part application of Ser. No.: 08/186,327 filed Jan. 24, 1994, now U.S. Pat. No. 5,578,314 on Nov. 26, 1996.

BACKGROUND OF THE INVENTION

Field of Invention

The current invention concerns a biological tissue transplant coated with a stabilized multilayer alginate coating and a method for preparation of such stabilized multilayer coating. The method involves formation of the coating comprising three layers of the alginate with a polyamino acid barrier emplaced between a primary and a secondary layer. The secondary "halo" layer of soft gel is formed by a gel gradient created between weakly bound cross-linking gelling divalent cations of a soluble alginate used for the primary layer of the coating and non-gelling counter ions of a non-ionic alginate of the secondary layer of the coating. The tertiary layer of the coating is generated by dispersing a suspension of a biological tissue core coated with the primary and secondary layers into a gelling divalent cations solution. The method additionally involves emplacement of a thin and delicate polyamino acid polymer barrier for retention of biological tissue within the primary alginate layer of the coating during creation of the gel gradient followed by ionic exchange.

The method results in the transplant coated with the primary alginate layer surrounded by the thin polyamino acid polymer barrier, with the secondary layer of soft gel and with the tertiary layer formed by gelling the alginate with the divalent cations, thereby forming the outer layer of a non-fibrogenic coating.

BACKGROUND AND RELATED DISCLOSURES

Traditional medical treatments for functional deficiencies of secretory and other biological organs have focused on replacing identified normal products of the deficient organ with natural or synthetic pharmaceutical agents or with cell or organ transplants. For example, for treating insulin-dependent diabetes mellitus where the pancreatic islets of Langerhans are nonfunctional, the normal secretion of insulin by the islets in the pancreas can be replaced either by daily administration of synthetic or substitute insulin, or by transplantation of functional human or animal islets.

A successful cell or tissue transplant must be coated with a coating which will prevent its destruction by a host's immune system, which will prevent fibrosis, and which will be permeable to and allow a free diffusion of nutrients to the coated transplant and removal of the secretory and waste products from the coated transplant.

Attempts to transplant organ tissues into genetically dissimilar hosts without immunosuppression are generally defeated by the immune system of the host. Attempts to provide effective protective barrier coatings to isolate the transplant tissues from the host immune system have not generally proven to be medically practical because the coating materials were incompatible with the host system or were otherwise unsuitable. The encapsulation or coating processes developed previously have not yielded reproducible coatings having the desired porosity and thickness required for the transplanted tissue to have a long and effective functional life in the host.

A primary problem with these coated cell or tissue transplants is that they are treated as foreign objects in the host's body and subject to immune rejection or destruction.

To protect transplants from destruction by the immune response of the host animal, various attempts have been made to create a protective barrier between the transplant tissue or cells and the immunological components of the host's system. Science, 146:524–525 (1964) describes the microencapsulation of erythrocyte hemolysate and urease in semi-permeable polyamide membranes. However, these microcapsules did not survive for long when injected into the blood stream. Both the preparation of semi-permeable microencapsulated microbial cells and viable red blood cells, and also the possibility of using injections of encapsulated cells for organ replacement therapy were described in Acta Chem. Scand., 20:2807–2812 (1966) and in Can. J. Physiol. Pharmacol., 44:115–128 (1966).

Multiple attempts have been made to use alginates for coating of cells and tissues. Compositions of alginates and methods for purifying and fractioning alginates have been generally described in Composition and Properties of Alginates: Report No. 30, Norsk Institute for Tangog Tareforsking (Norwegian Institute of Seaweed Research) (1964); Acta Chem. Scand., 13:601–603 (1959); Acta Chem. Scand., 19:1221–1226 (1965); Acta Chem. Scand., 21:691–704 (1967); Acta Chem. Scand., 22:1989–1997 (1968); and Biotech. and Bioeng., 33:90–94 (1989). Correlations between the chemical and physical properties of alginate gel beads have been reported in Biotech. and Eng., 33:70–89 (1989).

Viable tissue and cells have been immobilized in alginate. capsules coated with polylysine (J. Pharm. Sci., 70:351–354 (1981)). An attempt to use these coated capsules in pancreatic islet transplantation to correct the diabetic state of diabetic animals was reported in Science, 210: 908–909 (1981). The methods described in the above reference, however, have not been able to achieve long term correction of diabetes in animals, and therefore have not been suitable for transplanting tissues, such as pancreatic islets, in humans.

Diabetes, 40:1511–1516 (1993) reported the prolonged reversal of the diabetic state of mice with xenografts of microencapsulated rat islets, using alginate-polylysine capsules. Substantial additional efforts are described in U.S. Pat. Nos. 4,673,566, 4,689,293, 4,789,550, 4,806,355, and 4,789,550, for example, to develop transplants encapsulated in calcium alginate capsules reacted with polylysine.

U.S. Pat. No. 4,744,933 describes encapsulating solutions containing biologically active materials in a membrane of interreacted alginate and polyamino acid.

U.S. Pat. No. 4,696,286 describes a method for coating transplants suitable for transplantation into genetically dissimilar individuals. The method involves coating the transplant with a surface-conforming bonding bridge of a multi-functional material that binds chemically to a surface component of the transplant, which is enveloped in a semi-permeable, biologically compatible layer of a polymer that binds chemically to the bonding bridge layer. A disadvantage of this method is that it relies upon specific interaction of the first polymer coating with acidic residues of proteins on the cell surface and thus may not provide complete coverage of tissues, particularly if other tissues are adhering to the tissue particles (e.g., acinar tissue on islets) and interfering with the desired bonding.

The use of calcium alginates for immobilization of microbial cells and enzymes is described in J. Appl. Microbiol., 1:291–296 (1975) and *Biotech. and Bioeng.,* 19:387–397 (1977). Additionally, *Biotech. Tech.,* 2:271–276 (1988) describes methods for coating living cells in an outer membrane of calcium alginate by dropping a cell-containing calcium solution into an alginate solution and further incubating the capsules in a calcium solution.

*Lab. Invest.,* 90:6204–6205 (1990) describes an angiogenesis model using tumor cells entrapped in alginate beads where a spray of sodium alginate-cell suspension was contacted with aqueous calcium chloride solution to form calcium alginate beads.

Although alginates have been applied to coating food and pharmaceutical products, the use of alginates for coating living cells to produce a non-immunogenic coating which allows for long-term viability and function of the transplanted cells in a host animal has heretofore not been successful. Those working in this field have recognized that it is necessary to purify alginates for cell coating applications. For example, filtration has been suggested as a means to remove fibrotic fucan- and polyphenol-rich and other particulate contaminants. However, even such purified alginates themselves have been considered to be immunogenic. *Trans. Proc.,* 23:758–9, (1991) describes fibrous overgrowth of implanted alginate microcapsules in large animals. The study found that commercial alginates are often contaminated with polyphenols and other immunogenic materials and, even when purified by the methods employed, the commercial alginates having high mannuronic acid content were found to remain immunogenic and capable of activating macrophages in vivo, resulting in production of fibrotic overgrowth. *Cell Trans.,* 1:165 (1992) corroborates the above findings and suggests that all alginates are inherently fibrogenic even when purified by methods employed in these studies. Others have suggested that a reason why the alginates are not biocompatible is that high mannuronate alginates stimulate human monocytes to produce cytokines and enhance macrophage migration cytokines (*J. Immunother.,* 10:286–291 (1991), and *Carbohydrate Research,* 243:211–216 (1993)).

Despite recognition in this field that purified alginates might be used for coating cells, long term fully non-immunogenic coated cell or tissue transplants have not been achieved at present. Alginate coatings produced so far are either too thin, too thick or their thickness is not uniform. For fully functional transplant, it is important that the coating has a uniform thickness of between 20–200 µm. Alginate coatings having a thickness of greater than 200 µm lack the permeability required for diffusion of nutrients and cell products through the coating in amounts sufficient for long term viability of the coated transplant while implanted in the host system. (*Horm. Met. Res. Suppl.,* 26:209–213 (1990)).

Therefore, a need continues to exist to provide transplant coatings which have a thickness within the acceptable limits of about 20–200 µm, which are not rejected by the host immune system and which permit long-term viability and functionality of the transplant.

U.S. Pat. No. 5,227,298 describes a method for introducing a second alginate gel coating to cells already coated with polylysine alginate.

Recently, purified alginate coatings have been successfully used to coat isolated pancreatic cells. Purification of these alginates was employed to remove phenolic and sulfate containing impurities and contaminants, which may be responsible for fibrogenicity of the nonpurified alginate. This new process for purification of alginates, purified alginate and their use for coating of pancreatic and hepatic cells, and other biological tissue is described in U.S. Pat. No. 5,429,821 issued on Jul. 4, 1995, incorporated herein by reference.

It would, therefore, be highly desirable to provide a biological tissue transplant coated with stabilized multilayer coating and a method for preparation of the stabilized multiple coating able to withstand mechanical handling and chemical or immune reaction without being destroyed within the host body, which coating would not provoke fibrogenic reactions and impair the transplant function.

It is, therefore, a primary object of the current invention to provide a biological tissue transplant coated with a stabilized multilayer coating and a method for preparation of such multilayer coating. The new stabilized multilayer coating has a thickness between about 20–200 µm, is non-fibrogenic and does not cause immune reactions destructive to the transplant functionality.

All references and patents listed in this application are incorporated herein by reference in their entirety.

SUMMARY

One aspect of the current invention concerns a biological tissue transplant coated with a stabilized multilayer alginate coating suitable for transplantation.

Another aspect of the current invention is a transplant coated with a primary layer of the alginate surrounded by a thin polyamino acid polymer barrier, with a secondary "halo" layer of soft gel and with a tertiary outer coating of a non-ionic alginate gelled with a divalent cation.

Still another aspect of the current invention is a viable, functional and physiologically active biological transplant coated with a stabilized multilayer coating of the invention having a thickness between 20 and 200 µ and a permeability allowing the effective diffusion and release into the host's system of products secreted by the coated biological tissue as well as diffusion and transport of nutrients to the core of the transplant and transport of the waste produced by the core from the core.

Yet another aspect of the current invention is a method for preparation of the stabilized multilayer coating comprising a formation of several layers of the purified alginate coating wherein primary and secondary layers of coating are generated by exchange of divalent gelling cations of the primary layer with non-gelling counter ions of the secondary layer.

Still another aspect of the current invention is a method for preparation of a stabilized multilayer coating comprising generating a gel gradient between and displacement of weakly bound cross-linking gelling divalent cations of an alginate used for a primary layer of the coating with non-gelling counter ions of a non-ionic alginate of a secondary layer of the coating wherein displacement results in formation of a soft gel "halo" second layer of the coating.

Still yet another aspect of the current invention is the method wherein additionally a thin and delicate polyamino acid polymer barrier for retention of the biological tissue within the first alginate coating during the ionic exchange and creation of the gel gradient is emplaced between the primary and secondary layer of the coating.

Another aspect of the current invention is a method for preparation of a stabilized multilayer coating of biological tissue or cell transplants wherein alginate layers are formed by an ion exchange between a primary layer and a secondary layer and wherein the primary layer is separated from the secondary layer by a thin delicate polyamino acid barrier retaining a transplant tissue core within the primary layer during the ion exchange and wherein the secondary layer is a soft gel "halo" formed by an exchange of non-gelling ions, such as sodium, from a soluble alginate of the secondary layer for divalent cations, such as calcium, strontium or barium of the gelled alginate of the primary layer, and wherein said transplant coated with the primary and secondary layers is suspended in the non-ionic alginate and gelled with divalent cations solution to form a tertiary outer layer of the coating of the transplant.

Still another aspect of the current invention is a multistep method comprising steps:

(a) suspending and dispersing biological tissue in a solution of soluble alginate having a high molecular weight and high guluronate to mannuronate ratio using an electrostatic drop generator, air knife, spinning disc or other droplet forming device;

(b) capturing the droplets of the biological tissue suspended in alginate of step (a) in a divalent cation solution, such as calcium chloride, barium chloride, or strontium chloride, to produce gelled spheres wherein the biological tissue is suspended in a gelled primary alginate layer, such as in gelled calcium alginate, strontium alginate or barium alginate layer;

(c) briefly resuspending the spheres of step (b) in a dilute polyamino acid polymer solution, such as in 0.0005% to 0.005% of polylysine or polyornithine polymer having a molecular weight between about 20,000 and 450,000;

(d) removing an excess of polyamino acid polymer by rinsing the gelled spheres of step (c) in isoosmotic sucrose, saline or other isoosmotic non-ionic solution in a presence of soluble cations, such as calcium, barium or strontium added in concentration from about 6 mM to about 120 mM;

(e) resuspending the gelled spheres of step (d) in a high concentration of a soluble, medium molecular weight alginate having a high mannuronate to guluronate ratio, such as sodium alginate or a mixture of sodium alginate with 0.2–8% of agarose, dissolved in an ionic medium, such as saline, or non-ionic medium, such as sucrose, to form a gel gradient, and promote an exchange and partial displacement of divalent, cations of step (b), weakly bound to the gelled alginate of the primary layer, with the non-gelling sodium counter ions of the suspending alginate resulting in formation of the secondary "halo" layer of soft gelled alginate containing the divalent cation bound to the alginate layer surrounding the polylysine polymer barrier;

(f) quickly dispersing the suspension of step (e) as droplets using the air knife, electrostatic droplet generator or spinning disk;

(g) capturing the droplets of step (f) in a second cross-linking divalent cation solution, such as calcium chloride, strontium chloride or barium chloride, to form an outer tertiary layer of the coating of the gelled divalent cation alginate, such as calcium alginate, barium alginate or strontium alginate around the primary and secondary layers.

BRIEF DESCRIPTION OF DRAWINGS

FIG. 1 illustrates a method for production of biological tissue transplants coated with a multilayer alginate coating.

DEFINITIONS

As used herein:

"Biological tissue" means tissue cells, cell lines or biological active substances, which are submitted to the present method for encapsulation and form a core of the transplant. Examples of such cells, cell lines, and tissues are pancreatic islets, hepatic cells, neural cells, renal cortex cells, vascular endothelial cells, thyroid and parathyroid cells, adrenal cells, thymic cells, ovarian cells, allografts or xenografts. However, other types of cells or cell lines or biologically active substances intended to be implanted into the body of a host animal may also be utilized. These tissues or cells include, without limitation, tissue or cells removed from a donor animal, tissue or cells obtained by incubation or cultivation of donor tissues and cells, cells obtained from viable cell lines, biologically active products of cells or tissues, and the like. Examples of biological active substances are, among others, hormones, enzymes, DNA, RNA, peptides or proteins.

"Core" means the biological tissue, as defined above, which forms an internal part of the transplant.

"Transplant" means and includes a "core", as defined above, coated according to the invention. Any type of core for which transplantation is desired can be coated and transplanted according to this invention. Important tissues for transplants are secretory organ tissues, where transplantation from a donor organ to a host animal is desired to at least partially replicate the donor organ's action in the host system.

"Non-fibrogenic" means a coating which, when used to produce a transplant, does not induce autoimmune reactions, bio-isolation and transplant's core destruction by the host immune system through the process of fibrosis and macrophage overgrowth. In the case of encapsulated pancreatic islets, autoimmune reactions, bio-isolation and islet destruction may be determined by monitoring pancreatic islet transplant insulin production or by monitoring euglycemia, i.e., the maintenance of the normal level of glucose in a diabetic host. The stabilized non-fibrogenic alginate coating of the invention is suitable for coating of biological tissue according to this invention.

"Functional transplant" means the above transplant which is viable and functional in its normal way, that is, which produces or secretes products or hormones which it would normally produce endogenously in the donor body.

"Uniform thickness" means the thickness of the coating being between about 20 and about 200 μm wherein the thickness of the coating is preferably not below 20 μm and preferably not above 200 μm.

"Capsule", "sphere" or "droplet" means a coated core which becomes a transplant when coated according to the invention.

"Isotonic saline" means, unless specifically defined otherwise, 0.9% sodium chloride with 10 mM HEPES buffer.

"Calcium chloride solution" or "calcium solution" means, unless specifically defined otherwise, 1.7% calcium chloride dihydrate with 10 mM HEPES buffer.

"Divalent cation solution" means about 1% to about 2% solution of calcium, barium or strontium chloride dissolved in about 10 mM HEPES buffer or any other aqueous solution.

"Sucrose water" means, unless specifically defined otherwise, 9.25% sucrose in water with 10 mM HEPES buffer.

"High guluronate" or "guluronate-rich" means alginate containing a high ratio (>50%) of guluronate relative to mannuronate and typically having high molecular weight from about 80 to about 300 kilodaltons.

"High mannuronate" or "mannuronate-rich" means alginate containing a high ratio (>50%) of mannuronate relative to guluronate and typically having medium molecular weight from about 40 to about 120 kilodaltons.

"Barrier", "thin barrier" or "delicate barrier" means a very thin layer of polyamino acid polymer, such as polylysine or polyornithine or polyarginine polymer, having a molecular weight between about 10,000 and 450,000, crosslinked with a divalent cation of a primary coating wherein such barrier is generated by submerging the core coated with a primarly alginate layer in a polyamino acid polymer diluted to about 0.0005 to about 0.005% solution for less then 5 minutes.

"Halo" means a secondary layer of soft gel emplaced between a polyamino acid polymer barrier and a tertiary outer layer of alginate gelled with divalent cations. The halo is formed by exchange and partial displacement of divalent cations, such as calcium, strontium or barium, bound to the alginate of the primary layer with non-gelling counter ions of a non-ionic suspending sodium alginate or sodium alginate sucrose mixture where sodium partially displaces calcium, barium or strontium. The exchange occurs by diffusion of sodium ions into the primary alginate layer and displacement of divalent cations out of the primary alginate layer into the secondary alginate layer where the divalent cations are only weakly bound to the non-ionic alginate giving rise to a gel "halo" to form a substantially complete alginate "halo" layer around the primary layer covered with polyamino acid polymer barrier.

DETAILED DESCRIPTION OF THE INVENTION

The current invention provides biological tissue transplants coated with a physiologically acceptable stabilized multilayer alginate coating. The transplants of the invention are suitable for tissue or cell transplantation in human or other mammalian subjects suffering from cell or tissue malfunction or deficiency.

The invention also provides a method for preparation of the stabilized multilayer coating of biological tissue transplant involving formation of several layers of the alginate coating by creating a gel gradient between weakly bound cross-linking gelling divalent cations of a primary alginate layer and non-gelling counter ions of a suspending non-ionic alginate of a secondary layer of the coating. The formed gel gradient results in formation of an intermediate soft gel "halo" layer between the primary and the tertiary layers. The tertiary layer of gelled alginate is formed around the "halo" layer by dispersing the suspension of core coated with the primary and secondary layers in non-ionic alginate as droplets and gelling the non-ionic alginate with divalent cations.

The method additionally involves emplacement of a thin and delicate polyamino acid polymer barrier for retention of the biological tissue within the primary alginate layer during the ionic exchange and creation of the gel gradient by partial displacement of divalent cations with non-gelling counter ions.

The method results in a coated transplant containing a tissue or cell core coated with the primary alginate layer surrounded with a thin and delicate polyamino acid polymer barrier, with the secondary halo layer of soft gel and finally with a tertiary layer of gelled alginate to form the outer coating. The coating of the invention provides more complete and uniform coating for biological tissue than any other coating known before.

The present method differs substantially from all previously known tissue transplants coated with alginate and/or with polylysine. The gel gradient which is generated between the primary layer and the secondary non-ionic alginate layer allows the formation of a "halo" layer, providing an additional intermediate (secondary) layer between an inner primary and outer tertiary layer of gelled alginate of the multilayer coating. The "halo" layer thus provides additional protection for and uniformly covers any exposed area of biological tissue.

I. Multilayer Coating Method

The method of the invention comprises applying a uniform multilayer alginate coating to a core of the biological tissue, cells or other particles. The method is novel in that it relies upon exchange and partial displacement of divalent cations ($Ca^{++}$, $Br^{++}$ or $Sr^{++}$) weakly bound to a soluble alginate of high molecular weight used for the primary layer of the coating with non-gelling counter ions ($Na^{++}$) of a soluble non-ionic suspending alginate having a medium molecular weight. This exchange or partial displacement gives rise to a gel gradient extending from the primary layer of the coating into the suspending alginate of the secondary layer to form the primary alginate layer around the core.

An extremely delicate polyamino acid polymer barrier, such as polylysine polymer, is emplaced around the primary layer to retain the cells within the primary alginate layer during the ionic exchange and partial displacement resulting in creation of the gel gradient. This fragile polyamino acid polymer barrier crosslinks with the divalent cations of the soluble alginate and protects the core from being displaced from the soluble alginate layer during the gel gradient formation when the soluble alginate of the primary layer becomes liquified.

During the ionic exchange and partial displacement the polymer barrier collapses around the core and protects it. During this phase the calcium alginate gel is formed and extends through and beyond the primary calcium alginate layer, through the porous polyamino acid polymer barrier and into a soluble sodium alginate of the secondary layer. Extrusion of the gel-coated cores through a droplet forming device, and the capture of the formed droplets in the polymerizing divalent cation solution results in stabilized three layer coatings forming the initial primary layer, secondary "halo" layer comprising calcium gel gradient, and outer tertiary layer of gelled sodium alginate. The gel gradient assures that a uniformly thick alginate membrane surrounds the biological tissue/particles core.

This total coverage of the core cannot be attained utilizing the alginate polylysine encapsulation disclosed by prior art. None of the previously described methods utilizes such an ion exchange reaction and thin polyamino acid polymer coating, or produces such a complete alginate covering membrane.

Briefly, cells or other particles are suspended in a soluble, high molecular weight, guluronate-rich alginate about 0.1 to 10%, preferably 0.9% and dispersed by any dispersing means such as air-knife, spinning disc droplet generator, or electrostatic droplet generator. The dispersed droplets containing cells or other particles are captured in a gelling solution of cross-linking divalent cations such as ($Ca^{++}$, $Sr^{++}$ or $Ba^{++}$), of about 0.001 to about 0.120M or a combination of cations. The gelled droplets are resuspended briefly for less than 5 minutes in a very dilute concentration between about 0.0005 and about 0.005% of polyamino acid, such as polyornithine or, preferably, polylysine polymer, in the presence of soluble cations at concentration from about 6 mM to about 120 mM. The dilute polymer is then removed and the cells are rinsed with normal saline containing divalent cations, such as $Ca^{++}$, $Ba^{++}$, $Sr^{++}$, or their combination in concentration from about 6 mM to about 120 mM. The saline is removed and the coated cells or particles are then resuspended in a high concentration of soluble, medium molecular weight, mannuronate-rich alginate from about 0.1 to about 10%, preferably about 0.9% dissolved in an ionic or non-ionic medium. The divalent cations, such as calcium, weakly bound to the primary gelled alginate layer, exchange and are displaced with the non-gelling counter ions, such as sodium, of the soluble suspending alginate of the secondary layer. A thin layer of gelled alginate is formed around each coated cell group or particle by this exchange. The exchange takes place through the polymer net which holds the core in place during the weak gel formation. This exchange may result in collapse of the primary coat and reduce its volume when the concentration of sodium of the secondary alginate is too high, because calcium is responsible for rigidity of the primary alginate. After the ion exchange and gel formation steps, the spheres formed are dispersed by a droplet generating device. The dispersion is done within 30 seconds to 10 minutes from suspending the spheres coated with primary alginate covered with polymer barrier in the second alginate. The resulting droplets are captured in a cross-linking divalent cation solution, such as in calcium chloride, barium chloride or strontium chloride or other suitable salt in concentration from about 0.001 to about 0.120M, to form the tertiary layer of gelled alginate around the primary layer covered with the polymer barrier and the second "halo" layer of the calcium/gel gradient. The capture of the formed droplets in polymerizing divalent cation solution in any suitable divalent cations results in formation of stabilized three-layer coatings.

The alginate used for the primary layer is typically soluble and contains a high molecular weight guluronate while the alginate used for the secondary layer contains medium molecular weight mannuronate. However, any other suitable alginate may be advantageously used as the first alginate, The soluble non-ionic alginate used for the primary layer typically contains a high ratio of guluronate to mannuronate, and the alginate used for second alginate has a high ratio of mannuronate to guluronate and is typically of medium molecular weight. Similarly, this alginate may be substituted with another suitable alginate. Alternatively, the mannuronate-rich alginate may be used as the primary coating and the guluronate-rich alginate may be used as the second alginate. It is preferred that the first and second alginates are not the same, that is if one has high molecular weight, the other has medium molecular weight. The use of all alginates, whether commercially available or specifically prepared, whether purified or not is within the scope of this invention as long as these alginates are suitable to produce multilayer coatings of core material. Alginates are described in greater detail in Section III.

Extrusion of alginate cells or tissue cores suspension for the primary and tertiary layer formation is through any suitable droplet forming device, such as, for example, an air knife, electrostatic droplet generator or spinning disk, described in greater detail in Section IV.

Figure 1A:
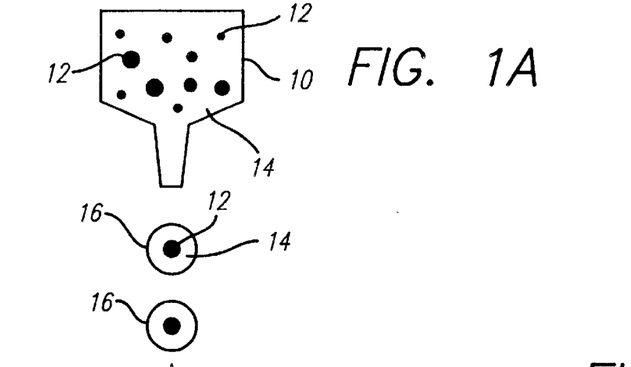
FIG. 1A shows biological tissue cores suspended and dispensed in alginate.
Figure 1B:
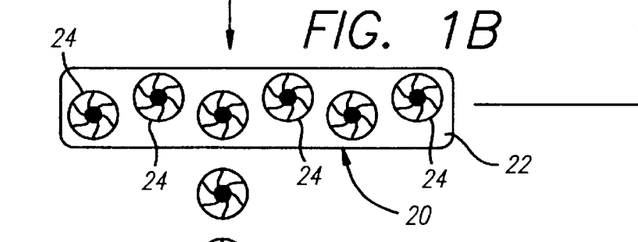
FIG. 1B shows a container containing a gelling solution of cross-linking divalent cations for gelling alginate.
Figure 1C:
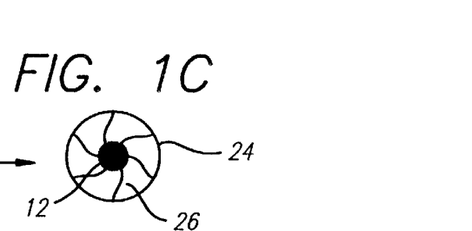
FIG. 1C shows in detail a sphere containing a core coated with a primary layer of the gelled alginate.
Figures 1D, 1E:
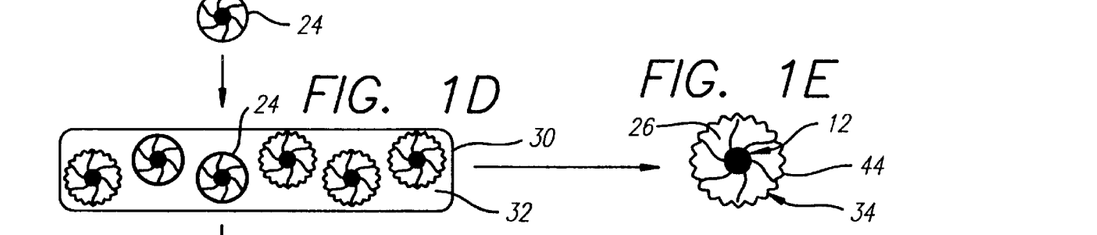
FIG. 1D shows multiplicity of spheres coated with primary alginate layers resuspended in a dilute solution of polylysine.
FIG. 1E shows in detail a sphere coated with the alginate and with a thin polylysine coating.
Figure 1F:
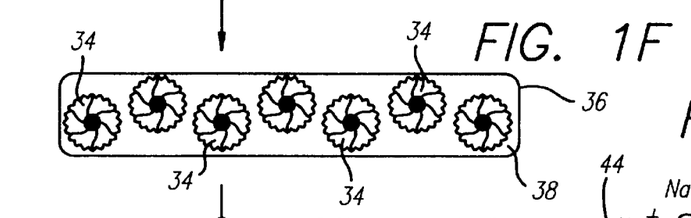
FIG. 1F shows multiplicity of spheres coated with the alginate and polylysine in a container containing divalent cations.
Figure 1G:
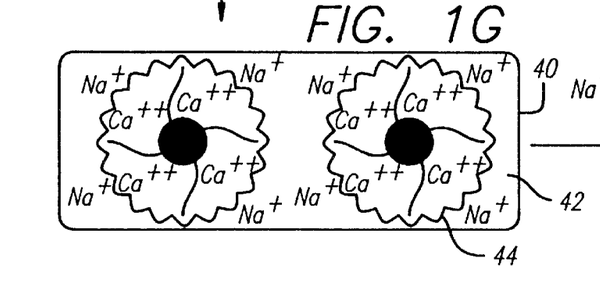
FIG. 1G shows in detail ionic conditions preceding the ionic exchange between the spheres and surrounding medium.
Figure 1H:
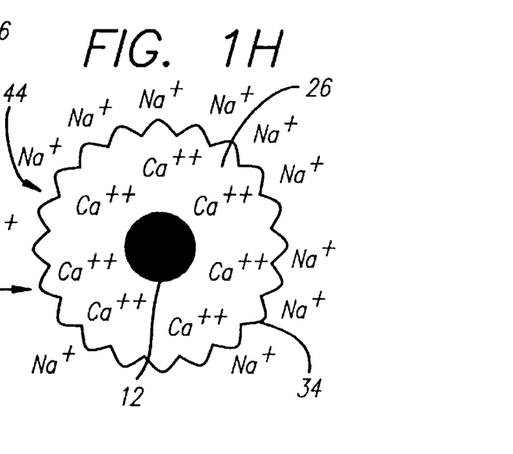
FIG. 1H shows in detail the ionic conditions between the sphere gelled alginate containing calcium ions and between the surrounding medium containing sodium ions.
Figure 1I:
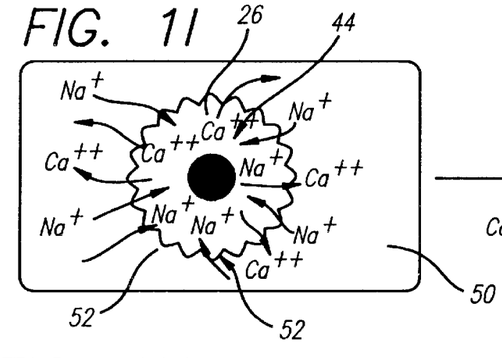
FIG. 1I shows a gel gradient and ionic exchange of sodium ions for calcium ions.
Figure 1J:
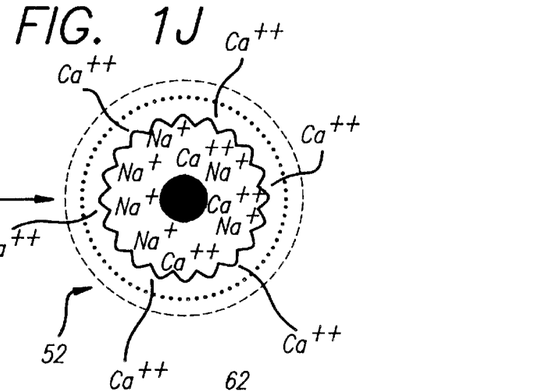
FIG. 1J shows in detail the actual ionic exchange proceeding between the internal gelled alginate and external medium.
Figures 1K, 1L:
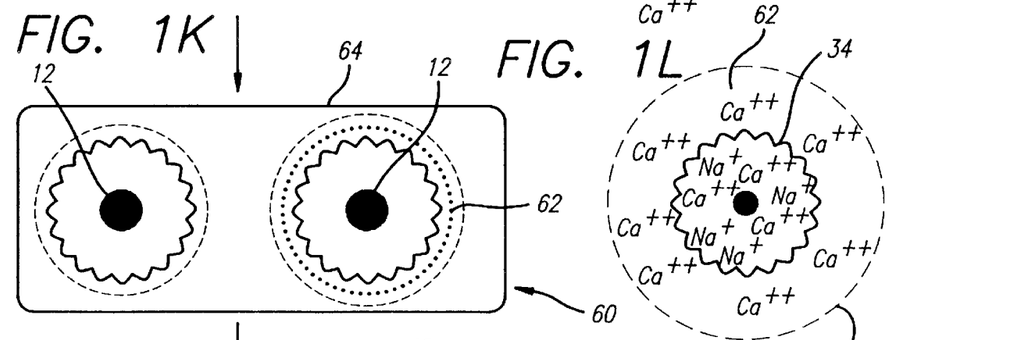
FIG. 1K shows a formation of an intermediary halo layer.
FIG. 1L shows a formation of the halo layer in greater detail.
Figures 1M, 1N, 1O, 1P:
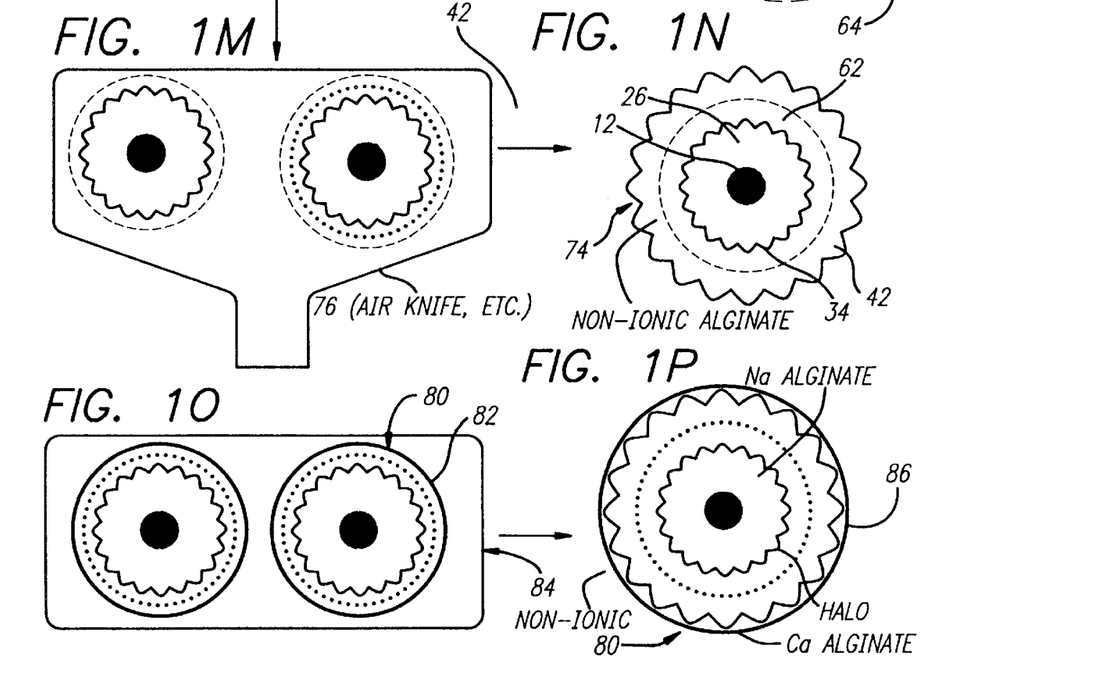
FIG. 1M shows a droplet generating device for dispersion of spheres coated with the halo layer in non-ionic sodium alginate solution.
FIG. 1N shows a transitional state of one sphere following its extrusion from the droplet generator.
FIG. 1O shows formed coated droplets captured in the gelling solution to tel a layer of a second alginate.
FIG. 1P shows a transplant coated with a stabilized multilayer coating.

The method for formation of multilayers coating of the invention is shown in FIGS. 1A through 1P.

FIG. 1A shows a biological tissue core (12) suspended in a soluble, high molecular weight, guluronate-rich alginate (14) and dispersed by some means, i.e., air-knife, spinning disc droplet generator, or electrostatic droplet generator (10). The dispersed droplets (16) containing the core suspended in the soluble alginate are captured in a container (20), seen in FIG. 1B, containing a gelling solution (22) of cross-linking divalent cations such as calcium chloride, barium chloride or strontium chloride. This results in formation of spheres (24) coated with the primary layer of the gelled alginate (26) such as, preferably, calcium alginate, barium alginate, strontium alginate or other suitable divalent cation alginate. Detailed structure of the sphere (24) is seen in FIG. 1C. The excess cations are removed by washing the spheres in saline.

The spheres (24), as seen in FIG. 1D, coated with the primary alginate layer (26) are transferred into a container (30) and resuspended briefly, for less than 5 minutes but preferably for 1–3 minutes, in a very dilute solution of polyamino acid, preferably polylysine, polymer (32) having molecular weight from about 10,000 to about 450,000, having a concentration of the polymer from about 0.0005% to about 0.005% dissolved in saline or calcium chloride 6 mM to 120 mM. This step is preferably carried out in the presence of soluble cations, for example, calcium, at concentrations from about 6 mM to about 120 mM used as a polymer divalent.

An extremely delicate polymer coating (34), as seen in detail in FIG. 1E, is formed around the primary alginate layer to retain the core within the primary alginate layer during the next step which includes ionic exchange, creation of the gel gradient and displacement of weakly bound calcium ions with sodium ions of the suspending alginate, as seen in FIGS. 1F through 1J.

The diluted polymer is removed and the spheres are rinsed in a container (36), seen in FIG. 1F, containing a solution (38) of normal saline or sucrose water and divalent cations present in concentration from about 6 mM to about 120 mM.

The coated spheres (34) are then transferred into a container (40), seen in FIG. 1G, containing a high concentration of soluble, medium molecular weight mannuronate-rich alginate, such as sodium alginate, dissolved in an ionic or non-ionic medium such as sucrose water, resulting in spheres (44) suspended in the alginate (42) creating milieu of divalent cations being present within the spheres (44) and of their counter ions, preferably sodium ions, present in the surrounding alginate (42). Detailed conditions of the milieu and the spheres structure is seen in FIG. 1H. These are the conditions immediately before the gel gradient began to occur.

FIG. 1I shows the generation of the gel gradient and exchange of internal calcium ions of the spheres (44) for sodium ions present in the soluble alginate (42) wherein some of the cations ($Ca^{++}$), weakly bound to the primary gelled alginate layer (26), exchange with the non-gelling counter ions ($Na^+$) of the soluble suspending sodium alginate (42) resulting in partial displacement. For the sake of better illustration, this is shown to happen in the separate container (50). In reality, there is no transfer of the spheres from one container (40) to the second container (50). These two figures and two containers only illustrate the change in the ionic state during the ionic exchange and formation of the gel gradient. As seen in FIG. 1I and in more detail in FIG. 1J, resulting spheres (52) underwent the partial ionic exchange in the primary layer of calcium ions with sodium. Thus the primary layer of alginate originally gelled with calcium ions has at this stage changed to sodium alginate covered with the polylysine barrier. Resulting sodium alginate still contain some calcium ions as the exchange between calcium and sodium is only partial and depends on the concentration of sodium ions in the second alginate.

Such exchange results not only in the change in the primary layer but also generates the secondary "halo" layer, again for the sake of clarity presented in separate FIG. 1K and in greater detail in FIG. 1L as structures (64), seen here in container (60). At the same time when the ionic exchange happens between the primary layer and the suspending alginate (42) when calcium ions are partially displaced by sodium from the primary layer alginate they enter the suspending alginate layer (42) and change it to a soft gel forming a structure resembling a "halo" surrounding this polymer barrier. The "halo" alginate layer (62) is generated by weak binding of calcium to non-ionic alginate. During this step when the chemical and physical properties of the gel change, the polylysine polymer barrier (34) retains and restrains the core within the primary alginate coat (26) resulting in spheres (64) seen in FIG. 1L.

Thus, a layer of thin gelled calcium alginate (62) is formed around each alginate/polylysine coated core. The above described ion exchange takes place through the polymer net which holds the core in place during the thin gel (62) formation. The calcium alginate gel seeps through and extends from the primary alginate layer, through the porous polymer layer and into the soluble sodium alginate. This exchange may result in a collapse of the primary layer as its gel consistency changes and also in reduction of its volume, if the sodium of the second alginate concentration is higher than that of the primary alginate. Therefore, the emplacement of a very thin and delicate polyamino acid polymer barrier represents a very important element of the multilayer coating of the invention. When there is a high $Na^+$ concentration in the soluble sodium alginate, the delicate polymer layer (34) can collapse around the core but it does not break. The thin and delicate polymer layer permits the ionic exchange. The polymeric nature of the barrier assures that it will not break and therefore it protects and constrains the core within the primary alginate layer regardless of the gel consistency at any time.

After the ion exchange, displacement of calcium ions by sodium ions and after secondary "halo" layer formation, the spheres (64) suspended in non-ionic sodium alginate solution (42) are dispersed by a droplet generating device (76), as seen in FIG. 1M. Its transitional state is shown in FIG. 1N showing the droplet extruded from the droplet generator where the sphere (74) contains the core (12) surrounded by the primary alginate coating (26) surrounded by the polymer barrier (34) and then surrounded by the "halo" (62). The resulting droplets (74) are captured in a container (84) seen in FIG. 1O containing a cross-linking divalent cation solution (82) to form the tertiary layer (86) of gelled second alginate around the primary layer and secondary layer resulting in transplant (80) coated with the stabilized multilayer coating, as seen in FIG. 1P.

In a preferred embodiment, the alginate solution is a sodium or potassium alginate solution, and the gelling solution contains a concentration of divalent ions sufficient to gel the alginate. The alginate solutions contain alginates preferably having mannuronate to guluronate moiety ratios of from 1:6 to 6:1, and preferably are free from impurities which would impair the viability and longevity of tissue transplants.

II. Tissue Suitable For Multilayer Coating

Any type of tissue, cells or cell lines for which transplantation is desired can be coated and transplanted according to this invention. Specific tissues, cells and particles suitable for multilayer coating are listed in definitions under the term "core".

Important tissues for transplants are secretory organ tissues, where transplantation from a donor organ to a host animal is desired to at least partially replicate the donor organ's action in the host system. Preferred donor tissue are pancreatic islets, hepatic cells, neural cells, renal cortex cells, vascular endothelial cells, thyroid cells, adrenal cells, thymic cells and ovarian cells and cell lines. For secretory tissues such as pancreatic islets, the thickness of protective coatings is uniform and in the range of from about 20 to about 200 $\mu$m. The coatings also have the permeability required to permit effective diffusion of nutrients and other essential biological materials to the transplanted tissues and passage of transplant's products into the host system. The coatings are non-fibrogenic and protect the core of the transplant from immunologically effective concentrations of agents of the host immune system.

III. Alginates and Purified Alginates

Alginate is a linear polymer of mannuronic and guluronic acid residues. These residues are arranged in blocks of several adjacent guluronic acid residues, forming so-called guluronate blocks, and blocks of adjacent mannuronic acid residues, forming so-called mannuronate blocks. The mannuronic and guluronic blocks are interspersed with blocks of alternating guluronic and mannuronic acid residues forming heterogeneous or mixed blocks.

Monovalent cation alginate salts, such as sodium or potassium alginate, are soluble. Most divalent cations, such as calcium, strontium or barium interact with alginate to form gels. Because of the higher affinity of these divalent cations for guluronate compared with mannuronate blocks and because of steric considerations, cooperative binding of gelling divalent cations to guluronate within guluronate blocks provides the primary intermolecular crosslinking responsible for formation of stable alginate gels. Mannuronate and mixed blocks are not crosslinked due to their weaker affinity for the crosslinking divalent cation, but function as flexible interconnecting segments between interacted guluronate blocks. The resulting gel structure has the appearance of an egg box, as it is frequently called.

Different divalent cations have different affinities for mannuronate and guluronate and thus are differentially susceptible to exchange by other monovalent or divalent cations. Likewise, depending on the molecular weight, the number of residues per block and the overall ratio of guluronate to mixed or mannuronate blocks, different alginates have different susceptibilities to undergo ion exchange reactions.

In the present invention, an initial fibrogenic alginate preparation is purified by any suitable means to yield a non-fibrogenic alginate suitable for coating cells. In alternative, a commercially available alginate which is already purified can be used as long as it is substantially non-fibrinogenic. Suitable initial alginate preparations are preferably obtained by isolating alginates from brown algae and are readily commercially available.

One way to purify the alginates is to contact the initial alginate preparations with a divalent metal-ion chelating agent to remove divalent metal ions, and then contact the alginate with high surface area, bleached, activated carbon. The carbon adsorbs polyphenols together with associated protein and fucose moieties. After treatment with carbon, the alginate is precipitated from solution, washed and then filtered to remove additional impurities and to provide the non-fibrogenic alginate of the present invention. However, any other suitable purification method may be advantageously utilized.

Typically, to prepare the non-fibrogenic alginate of the invention, an initial alginate preparation is dissolved in water or buffer, preferably containing a divalent metal-ion chelating compound such as ethylenediamine tetraacetic acid (EDTA), EGTA or sodium citrate, among others, and then contacted with a high surface area, activated carbon to remove any polyphenols and other organic associated contaminants present by adsorption. About fifty grams of alginate is usually dissolved in about 1 to 10, and more preferably about 3 to 8 liters, of water. Suitable activated carbon includes any high surface area activated carbon having a particle size of about 100 mesh or finer. Preferably, very fine activated carbon powder having a surface area of at least about 1,000, and preferably at least about 1,500 $m^2/g$, may be used. Suitable activated carbon is commercially available.

The activated carbon is preferably bleached to oxidize and remove organic contaminants prior to use. The activated carbon may be bleached using a known bleaching agent such as sodium hypochlorite, and the like. The carbon may be bleached by stirring it with a dilute solution of the bleach for a time sufficient to remove any contaminants from the surface of the carbon. This is accomplished by stirring the activated carbon with about 0.005 to 0.50M, and more preferably about 0.08 to 0.10M, sodium hypochlorite solution for about 5 to 30 minutes, preferably about 10 to 20 minutes, which is sufficient to oxidize the activated carbon. After oxidation, the activated carbon may be removed from the dilute bleach solution by centrifugation or filtration, washed with ethanol and water, and dried. The ratio (w/w) of initial alginate to activated carbon is usually about 1:1 to 1:20, more preferably about 1:2 to 1:8. The amount of activated carbon may be adjusted as necessary to insure the removal of contaminants sufficient to achieve the minimum amounts permitted by this invention.

The alginate solution and bleached carbon are contacted by simple mixing, shaking or rolling, and the bleached carbon is then removed by conventional centrifugation and filtration. Preferably, the filtration is conducted using sequentially finer sub-micron filters.

A monovalent cation salt solution is then added to the filtered alginate solution in an amount sufficient to allow precipitation of the alginate by addition of ethanol. Any soluble monovalent cation salt may be used. Sodium chloride solution of about 0.05 to 1.0M is preferred.

The alginate is then precipitated from the resulting solution by addition of ethanol with stirring. Generally, the ratio (v/v) of ethanol to alginate solution is about 0.25 to 2.0, and preferably about 0.5 to 1.5. The precipitated alginate is then recovered by filtration, washed with ethanol and dried to remove any traces of ethanol.

The alginate obtained as described above is directly suitable for coating a transplant tissue or cells. Moreover, it is possible, if desirable, to further purify the alginate or chemically modify the properties of the alginate to tailor the alginate coating to provide specific properties. Important properties of the alginate coating materials include, for example, a well defined and controlled pore size providing a desirable permeability of the coating for diffusion of materials to and from the encapsulated core; the coating thickness of each layer; the viscosity of coating solutions and the mechanical strength of the coating.

The average molecular weight and overall mannuronate to guluronate molar ratios are initially substantially determined by the origin of the material, but may be further adjusted by physical and chemical methods. Typically, the molecular weight of suitable alginate is within the range from 20–500 kilodaltons. The molecular weights may be reduced, for example, by partial acid hydrolysis, thermal degradation or sonication. High molecular weights may be obtained by controlled precipitation methods with concomitant alteration of uronic acid composition, or by dialysis, molecular filtration, or gel exclusion chromatography. The mannuronate to guluronate ratio and sequence distribution is typically increased or decreased by selective precipitation or solubilization by monovalent or divalent metal cations, organic solvents or acids. Adjustment of these characteristics provides optimum alginate properties for coating of different tissue transplants.

The appropriate concentration of an alginate in solution is a function of the physical properties of the alginate. At very low concentrations the coating morphology is poor, resulting in ineffective coatings. At very high concentrations, the viscosity is too high to form coatings of appropriate thickness. Preferably, the relative amount of mannuronate and guluronate in the alginate is from 1:6 to 6:1 and can be adjusted by, for example, dissolving precipitated alginate in a solution, for example about 0.05 to 1.00M potassium chloride, to redissolve guluronate-rich fractions while mannuronate-rich fractions are left in the precipitate. The insoluble material may be collected by centrifugation. The redissolved guluronate-rich material is then reprecipitated by addition of ethanol. By repeating this process, different relative proportion of mannuronate and guluronate in the alginate is obtained.

Homopolymeric polymannuronate and polyguluronate alginate sequences are generally acid-insoluble, whereas alternating mannuronate-guluronate sequences are for the most part acid-soluble. By extracting the alginate with an acid solution of pH about 1.5 to 2.5, and preferably having pH about 2.0, it is possible to selectively solubilize alternating mannuronate-guluronate block-rich alginates. Additionally, mannuronate-rich alginates are preferentially solubilized relative to guluronate-rich alginates. The treatment of an alginate with an acidic solution, therefore, precipitates guluronate-rich alginates preferentially leaving mannuronate-rich and particularly alternating mannuronate-guluronate-sequence-rich alginates in solution. The separation of the precipitate from the solution thus provides both guluronate-rich and heterogeneous block and mannuronate-rich alginate fractions. The guluronate-rich alginate present in the solution is precipitated by the addition of calcium ions or ethanol. Alternatively, the guluronate-rich alginate can be obtained by precipitation of the guluronate-rich fractions with calcium ions while leaving the mannuronate-rich fractions in solution. After separation of the precipitate from the solution, the mannuronate-rich alginate fraction is precipitated from solution by addition of acid or ethanol. The proportions of acid and/or calcium precipitated materials is controlled by adjusting the pH and the calcium concentration, respectively.

It is also possible to obtain specific relative amounts of mannuronate and guluronate in the alginate coating by mixing different mannuronate-rich fractions and guluronate-rich fractions obtained as described above. By sequentially adding small portions of guluronate-rich material to mannuronate-rich material, the amount of guluronate in the overall alginate composition may be gradually increased, thereby increasing the number of divalent metal ion binding sites in the overall coating, increasing the structural rigidity of the coating, and producing larger pore sizes. For any particular mixture of mannuronate-rich and guluronate-rich fractions, the relative amount of mannuronate or guluronate in the alginate may be readily determined by NMR spectroscopy. The average molecular weight and porosity of the alginate coating can be adjusted by mixing mannuronate-rich and guluronate-rich fractions in different proportions.

The mannuronate to guluronate molar ratio of the coating polymer is typically from 1:6 to 6:1.

The current alginate coating is substantially free from fucose, polyphenol, protein and other impurities. The amount of fucose groups in the coating is, in general, less than about 0.2 micrograms per milligram of sodium alginate (even less than about 0.02 wt %) and the amount of polyphenol groups is, in general, less than about 2.0 micrograms of tannin-equivalents per milligram of sodium alginate, which corresponds to less than about 0.2 wt %.

All alginates described above and any and all their mixtures and combinations or any other suitable alginates are intended to be within the scope of this invention as long as these mixtures will result in a coating having the properties intended by the current method.

IV. Droplet Generating Devices

Any appropriate type of droplet generating device can be successfully utilized in the process of this invention. Examples of such droplet generating devices are the air knife, electrostatic droplet generator and a spinning disc droplet generator. An air knife device is described in U.S. Pat. No. 5,521,079 issued May 28, 1996, hereby incorporated by reference. An electrostatic droplet generator is subject of the patent application Ser. No. 08/422,032 filed on Apr. 14, 1995, which is hereby incorporated by reference.

A spinning disc droplet generator, such as, for example, described in copending application Ser. No. 08/234,290, incorporated by reference, comprises a rotating bead forming cup means for forming beads and projecting them outward, and a collection basin surrounding the bead forming cup means and axially concentric therewith. The collection basin is mounted for rotation about its central axis and positioned to collect beads projected outward from the bead forming cup means. Elevation adjustment means is connected to a coating apparatus for adjusting the alignment of the bead forming cup means with respect to the collection basin in the axial direction. The collection basin is connected to a first rotational drive means. The first rotational drive means includes speed adjustment means for adjusting the rotational speed of the collection basin. The bead forming cup means is preferably attached to a second rotational drive means, and the second rotational drive means includes second means for adjusting the rotational speed of the bead forming cup means. The elevation adjustment means can be a means for elevation of the second rotational drive means. The bead forming cup means typically has an axially concentric mixing chamber, the walls thereof forming an angle of less than 5° with the central axis of the bead forming cup means in a plane through the central axis thereof. The mixing chamber has an upper boundary from which a contiguous bead forming surface extends outward, the bead forming surface forming an angle with the central axis which is sufficient to establish surface contact with the droplets, The bead forming surface can form an angle with the axis thereof from about 0° up to less than 90° and preferably from 10° to 85° with the central axis of the mixing chamber in a plane through the central axis thereof. The surface of the bead forming surface can be smooth or textured and can have a coating which interacts with the beads to increase the surface-liquid interaction. For example, the surface can be roughened with fine abrasive (such as a fine sandpaper or steel wool) wiped across the surface in a radial direction or an angle thereto, or the surface can have radial grooves. The collection basin comprises a first annular channel having upper and lower rims extending inwardly toward its central axis, the lower rim thereof defining a second annular channel having an upwardly extending inner rim. The second annular channel comprises downwardly converging inner and outer surfaces. The second annular channel includes an annular trough having inner and outer boundaries, the inner surface extending upward from the inner boundary and contiguous therewith, and the outer surface extending upward from the outer boundary and contiguous therewith. The first annular channel has a substantially cylindrical bottom surface and said second rim extends to the bottom surface and is contiguous therewith. The collection basin can comprise a plurality of adjacent annular channels, each channel having upper and lower rims extending inwardly toward its central axis, each lower rim thereof defining a second annular channel having an upwardly extending inner rim. Preferably, the diameter of adjacent channels are not the same.

Any of the above-mentioned and other suitable droplet generating devices can be advantageously utilized.

V. Coated Transplants and Their Functionality

The transplants coated according to the invention were tested in animal models and in vitro studies.

Figure 2:
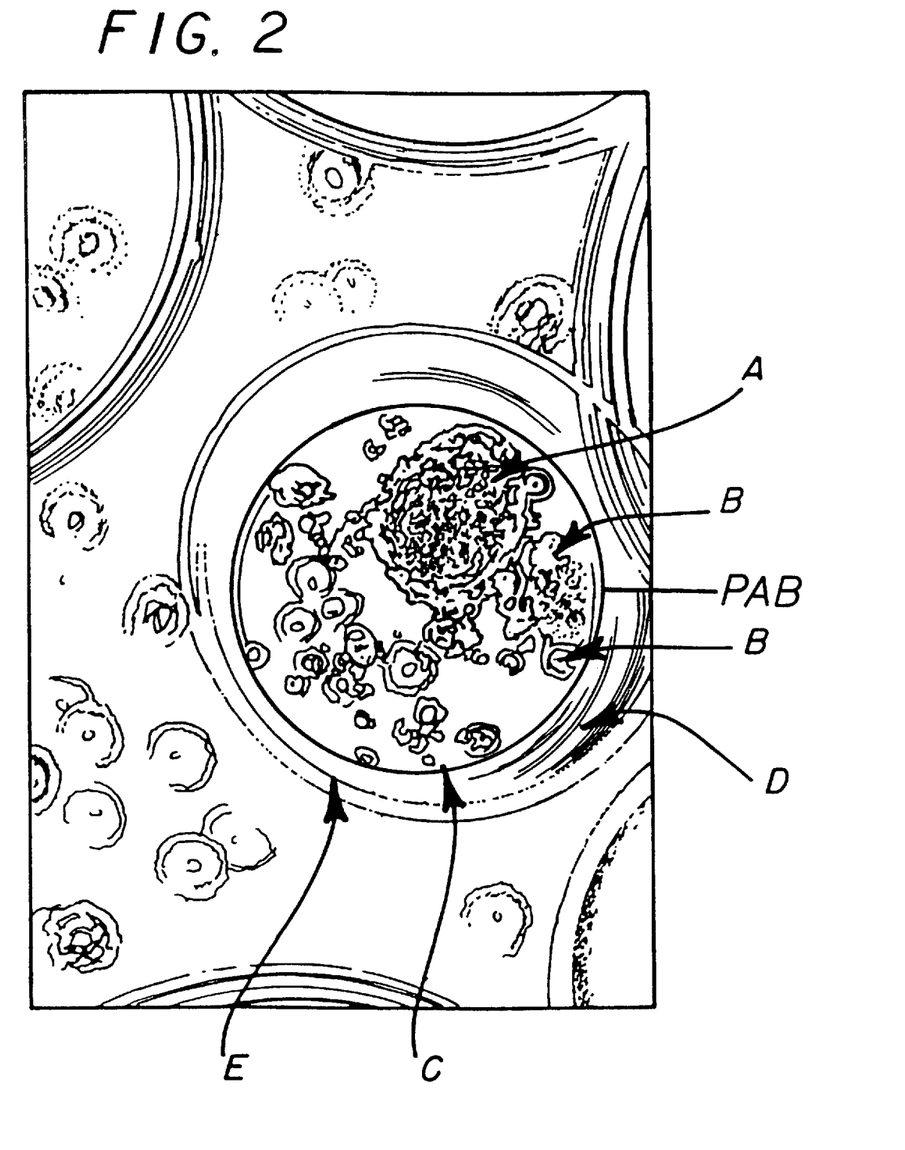
FIG. 2 is a drawing of an isolated pancreatic islet coated with a primary layer, a polyamino acid polymer barrier, a secondary "halo" layer and a tertiary gelled alginate layer.

The pancreatic islet transplant coated with stabilized multilayer coating according to the invention, as seen in FIG. 2, corresponds to the coated transplant (80), seen in FIG. 1.

FIG. 2 is a drawing representing an actual photograph of the pancreatic islet coated with a stabilized multilayer coating according to the method of the current invention. Pancreatic islet (A) and several individual pancreatic cells (B) form the transplant core. The core is enclosed in the primary layer of gelled alginate coating (C) surrounded by emplaced polyamino acid barrier (PAB) surrounded by the secondary "halo" layer (D) of soft gel formed by the displacement of calcium ions from the soluble alginate of the primary coating (C) with the sodium counter ions present in the secondary non-ionic alginate. The tertiary layer (E) is a non-ionic sodium alginate gelled with calcium ions.

The pancreatic islets transplants prepared according to the invention were tested in the dog diabetic model. Results of these studies are seen in FIGS. 3 and 4.

Figure 3:
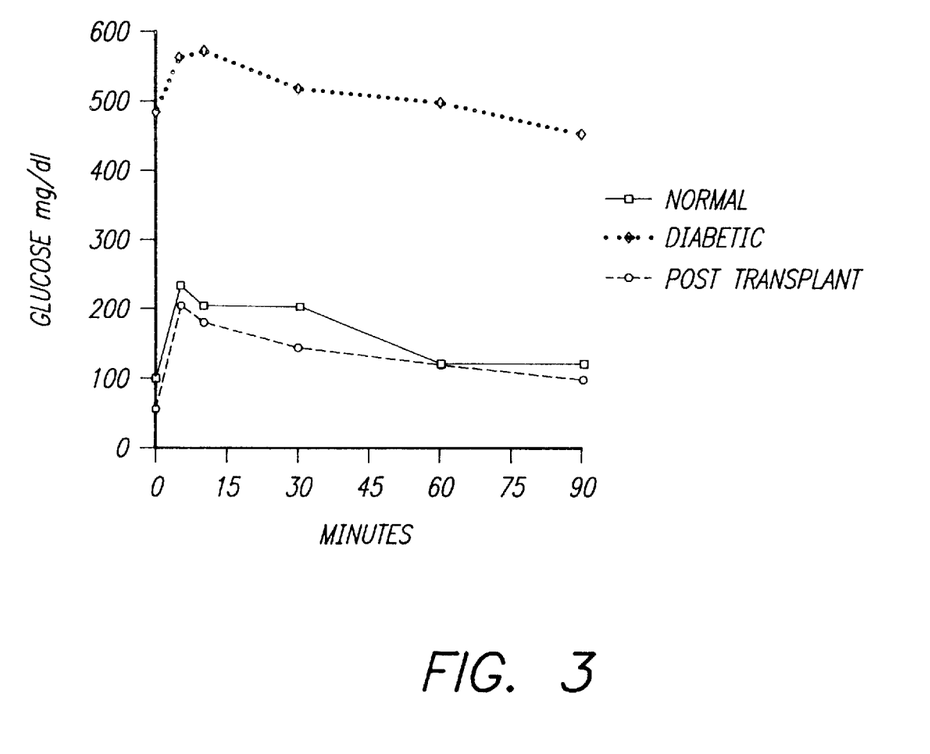
FIG. 3 shows comparative values of blood glucose values measured in normal dog, diabetic dog and diabetic dog after transplantation with dog islets coated with a stabilized multilayer alginate coating according to the invention.

FIG. 3 illustrates the blood glucose levels in the control nondiabetic dog, in the same dog made diabetic without transplant and in the same diabetic dog being injected with about 300,000 pancreatic islets coated according to the invention. The post transplantation dog was observed for 90 days following transplantation and at this time, it is still alive and continues to be euglycemic.

The dog's normal levels of glucose were determined before the dog was rendered diabetic by a pancreatectomy according to Example 9. The dog islets were coated with stabilized coating as described in Example 4. Approximately 300,000 coated islets were injected into the dog's peritoneal cavity. The dog transplanted with coated pancreatic islets became quickly, within a few minutes, euglycemic and followed the same course as that observed when it was normal, that is its glucose level corresponded to or was lower than those levels observed in the normal nondiabetic animal. The untreated diabetic dog without transplanted coated islets, as seen in FIG. 3, has shown highly increased (3–5 times) glucose levels. FIG. 3 shows the results of glucose levels up to 90 minutes.

Figure 4:
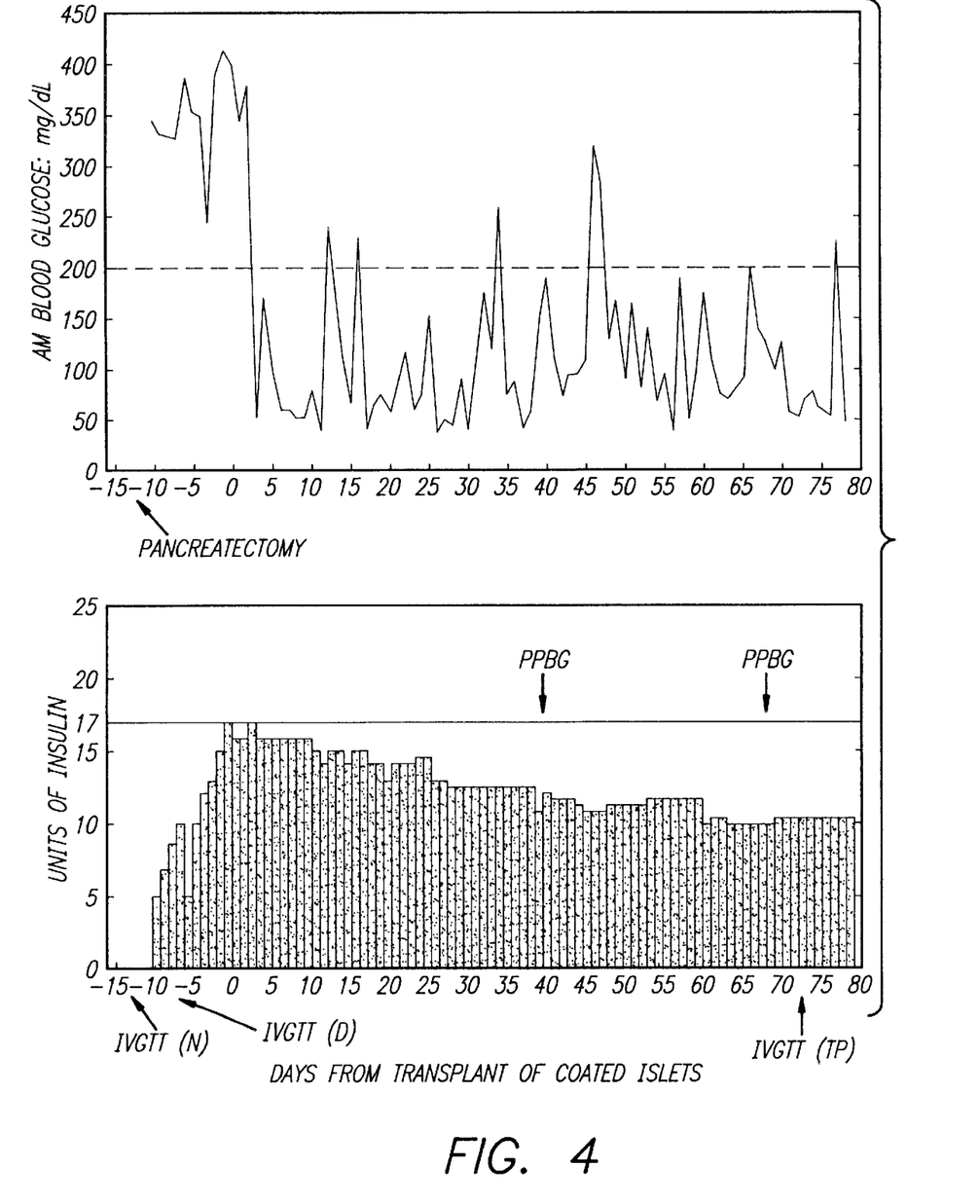
FIG. 4 shows survival, blood glucose levels, and levels of administered insulin in a diabetic dog transplanted with dog islet coated with a stabilized multilayer alginate coating observed for 80 days after transplantation.

FIG. 4 illustrates the results obtained with transplantation of dog pancreatic islets to the same experimental diabetic dog as seen in FIG. 3. Following surgery, the dog's blood glucose level increased to between 250 and 410 mg/dL and required up to 17 units of insulin to maintain a blood glucose level below 150 mg/dL. After transplantation at day 0, the dog's blood glucose level and insulin requirement began to decline consistently to levels of glucose around 200 and below 200 mg/dL, whereas the insulin requirement decreased to 11 units of insulin. These results represent a significant decrease (<0.001) of insulin requirement. On day 80, the animal required 11 units of insulin and maintained blood glucose below 200 mg/dL. The dog had intermittent elevation (day 45) in its blood glucose levels from about 100 mg/dL to about 300 mg/dL which was controlled within the next few days by reinjecting additional amounts of transplants.

The obtained results show that the stabilized multilayer coating of pancreatic islets provides functional replacement for a dysfunctional pancreas. When the transplants are implanted in sufficient amounts they are able to completely control the underlying disease.

Additionally, the stabilized multilayer coating was tested on several other types of cells and tissues. Calcitonin producing cells were coated according to the invention and their viability tested by using trypan blue/dye exclusion and alamar Blue assays. These assays demonstrated that there were viable cells and continued cell growth in the population. In vitro experiments were used to follow containment, growth and product secretion. The procedures are described in Example 10.

Similarly, hepatocytes were coated according to the invention and their viability and functionality was tested, as described in Example 11.

UTILITY

The transplants coated with multilayer coating according to the current invention are useful for treatment and correction of dysfunctions, deficiencies, and disturbances such as diabetes mellitus, hepatic failure, hypothyroidea, hypoparathyroidea, Cushings disease, hemophilia and others.

The multiple coating according to the current invention assures the immuno-resistance of the biological material such as coated cells or tissue, while at the same time preserving the functionality of the coated cells or tissue and diffusion of the secreted hormone or product of the cells or tissue and exchange of nutrients and secretion and waste products in and out of the formed coated capsules containing a core of biological tissue or cell.

The method can be used to coat any biologically active tissues or cells. All living tissues or cells which produce biologically active substances intended to be implanted into the body of a mammal host can be coated and implanted as coated transplants by using this method. These tissues and cells include, without limitation, tissue, cells and cell lines removed from a donor human or animal, tissue and cells, and cell lines obtained by incubation or cultivation of donor tissues and cells, cells obtained from viable cell lines, biologically active products of cells and tissues, and the like. Any type of tissue, cell or cell line for which transplantation is desired can be coated and transplanted according to this invention.

Important tissues for transplants are secretory organ tissues, where transplantation from a donor organ to a host animal is desired to at least partially replicate the donor organ's function in the host system. Preferred donor tissues are pancreatic islets, hepatic cells, neural cells, renal cortex cells, vascular endothelial cells, thyroid cells, adrenal cells, thymic cells and ovarian cells. However, other types of cells may also be utilized. The invention is particularly advantageous for coating pancreatic islets, hepatic cells, calcitonin producing islets and other endocrine tissues and cells.

Coating agents must be physiologically acceptable and non-toxic to the biologically active core being coated and to the host tissue. The coating must be non-fibrogenic. Coatings having an outer negative charge such as alginates are typically most suitable. The most preferred alginates are free from fibrogenic concentrations of fucose, sulfate, phloroglucinol and protein moieties and other impurities.

Implantation is typically by simple injection through a hypodermic needle having a bore diameter sufficient to permit passage of a suspension of coated cells therethrough without damaging the tissue coating. For implantation, the coated transplant tissues are formulated as pharmaceutical compositions together with a pharmaceutically acceptable carrier. Such compositions should contain a sufficient number of coated transplant capsules which can be injected into it mammal, animal and human subjects.

The number of transplants depends on the tissue and on the state of disease or purpose of the replacement. Typically, for example, the number of transplanted islets is within 10 to 30 thousand per kg of body weight. In animal studies, the dogs were transplanted with about 200–400 thousand coated islets. For human transplantation several million of pancreatic islets may be needed. The number for other cells, tissues or cell lines will be calculated depending on their function.

The invention offers several advantages over previously known and available methods for transplant coating.

Transplants according to the invention are coated with a stabilized and uniform coating of several layers. The biological tissue is contained within the first alginate layer which is stabilized with a thin polyamino acid barrier and surrounded by the "halo" soft gel and with outer gelled alginate. The new multilayer coating affords protection for and allows the cells or biological tissue to function normally. The coating's permeability allows the biological tissue product to diffuse to the host system and, at the same time, allows diffusion of nutrients to the core of the transplant as well as removal of the core waste product from the core.

The coating has a long functional life and has been shown to be non-fibrogenic and functional for 90 days in experimental dogs. The multilayer coating has a uniform thickness of between about 20 and about 200 μm which assures the normal functioning of the core and prevents the transplant from being destroyed by the immune reaction. The method of this invention provides coated transplants which are resistant to fibrosis, host immune rejections and other detrimental reactions upon implantation into a host. Transplants of cells coated with multiple layers of purified alginate substantially fail to produce fibrosis and when administered, for example, to diabetic animals, are able to correct an insulin deficiency for an extended period of time. The coating layers utilize purified alginates which do not provoke host immune reactions.

Another advantage of the current invention is that the novel multilayer coating of the transplant has a uniform thickness which can be applied to numerous cell or tissue cores in an efficient, convenient and reproducible manner. The multilayer coating procedure is efficient for the mass production of transplants having alginate coatings with a thickness of less than about 200 μm. Formation of a polyamino acid, such as polylysine polymer barrier stabilizes the first alginate coating and retains the biological tissue core within the first coating and a halo layer prevents exposure of the biological tissue core and protects the biological tissue from the host immune system.

Additionally, the current invention utilizes a very minute amount and dilute polylysine polymer emplaced within a multilayer coating comprising a "halo" layer. These layers obviate reactions such as the dissolution of calcium alginate gel by chelation of calcium. Such reactions may result in the presence of residual soluble alginate within the capsule which may leak from the capsule and cause a fibrotic reaction.

This invention is further illustrated by the following specific but non-limiting examples.

EXAMPLE 1

Method for Preparation of Stabilized Multilayer Coating

This example illustrates the method for formation of a stabilized multilayer alginate coating of cell and tissue transplants.

Dog pancreatic islets (approximately 300,000) were isolated as described in Example 3 and suspended in 2.5 ml of soluble alginate, according to Example 4, having guluronate to mannuronate ratio 6:1, prepared according to Example 2. The suspension was dispersed using the electrostatic generator as described in Example 4 and gelled by reaction with calcium chloride (6 mM). Obtained spheres were transferred into a solution of 0.005% polylysine polymer having molecular weight 200,000 for 4 minutes dissolved in 6 mM calcium chloride solution. After the formation of a thin layer of polylysine was observed, the polylysine was removed and the spheres were rinsed with isoosmotic sucrose in a presence of 60 mM of calcium chloride. The resulting spheres were resuspended in sodium alginate containing 2% of agarose dissolved in 2.5 ml sucrose to form a gel gradient. Exchange of calcium/sodium happened within 2–10 seconds after resuspension and the resulting spheres were then dispersed using the electrostatic droplet generator. Dispersed droplets were captured in 10 ml of 117 mM calcium chloride solution.

Specific and various conditions for coating and testing of dog islets thus prepared are described in following Examples 2–9.

EXAMPLE 2

Preparation of High Mannuronate and High Guluronate Alginate

This example illustrates preparation of alginates having high content of mannuronate (mannuronate-rich) or high content of guluronate (guluronate-rich) used as a first coating.

Eighty grams of protein alginate commercially available from Protan Biopolymers, Trondheim, Norway, were dissolved in 89 liters of water by rolling on a roller mill. The solution was filtered through a 50 micron mesh to remove particles, and then mixed on a roller mill with 320 g of bleached, activated charcoal with continued mixing for 30 minutes. The activated charcoal was then removed by centrifugation for 30 minutes. The resulting solution was sequentially filtered through filter paper, a 0.45 micron filter, a 0.22 micron filter and a 0.1 micron filter. Magnesium chloride (163 g) was then added to the solution and dissolved by rolling on a roller mill, followed by the addition of 210 ml of a 1.7% calcium chloride dihydrate solution and mixed by rolling on a roller mill for 30 minutes. The resulting solution was centrifuged for 30 minutes to produce an alginate pellet. The alginate pellet was dissolved in 3.0 liters of 0.1M EDTA, pH 7.0 by rolling on a roller mill. The pH of the solution was adjusted to pH 7.0, as needed. Sodium chloride (20 g) was then added to this solution and dissolved.

Alginate was precipitated from the solution by the addition of 5 L of neat ethanol, followed by centrifugation for 30 minutes to obtain an alginate pellet. The alginate pellet was then suspended in ethanol and tweezed apart with tweezers to insure complete washing of the sample. Excess ethanol was removed by squeezing and pressing the precipitate. The alginate precipitate was dried in an oven, under vacuum, at 60° C. 50 g low viscosity sodium alginate (LV Alginate, KELCO Div. of Merck & Co., San Diego, Calif.) isolated from *Macrocystis pyrifera* were dissolved in 5 liters of water and filtered through a 50 micron mesh to remove particulates. Tetrasodium EDTA (18.6 g) was added to the solution and dissolved. The solution was mixed on a roller mill with 200 g hypochlorite-bleached activated charcoal (Mallinckrodt activated charcoal powder) for 30 minutes to remove organic contaminants such as polyphenols. Activated charcoal was removed by centrifugation for 30 minutes. The resulting solution was sequentially filtered through filter paper, a 0.45 micron filter, a 0.22 micron filter and a 0.1 micron filter. Sodium chloride (30 g) was added to 5 L neat ethanol. The sample was centrifuged for 30 minutes to obtain an alginate pellet and the alginate pellet was suspended in ethanol and then tweezed apart with tweezers to insure complete washing of the sample. Excess ethanol was removed by squeezing and pressing the precipitate. The resulting precipitate was dried in an oven, under vacuum, at 60° C.

EXAMPLE 3

Preparation of Pancreatic Islet Suspension

This example illustrates the preparation of dog or rat islets in an alginate suspension.

Pancreatic islets were isolated from dog by collagenase digestion using the method described in *Can. J. Surg.*, 33:368, (1990). The final suspension of 37,000 isolated islets in 50 ml tissue culture medium (GIBCO CMRL-1066 with 25 mM HEPES, 10% Hy Clone FBS, 2 mM L-glutamine, 100 μg penicillin/ml, 100 μg streptomycin/ml) was gravity sedimented at room temperature for 15 minutes. The medium was diluted with isotonic saline by removing 25 ml medium and replacing it with 25 ml saline. The 15 minute gravity sedimentation was repeated. The supernatant was removed to 5 ml. The islets were transferred to a 15 ml conical centrifuge tube (Corning 430055) and diluted 1:3 by the addition of 10 ml saline. After a 10 minute gravity sedimentation, the supernatant was removed and the islets resuspended in 15 ml saline. The supernatant was removed to a final volume of 0.2 ml islets in saline. 0.05 ml of 3.44% sodium citrate dihydrate with 10 mM HEPES and 2.25 ml 1% high guluronate alginate (Example 1) was added to the islet suspension giving a final concentration of 14,000 islets in 0.9% alginate in saline with 10 mM HEPES and 6 mM citrate. The final suspension of islets ranges from 10,000–35,000 islets/ml of 0.7–1.0% alginate.

Pancreatic islets were isolated from 10 rats using the method described in *Diabetes*, 16:35 (1967). The 5,000 islets in 50 ml CMRL tissue culture medium were gravity sedimented at room temperature and washed with saline. The final supernatant was removed to 0.375 ml of islets in saline. 0.075 ml citrate and 1.05 ml 1% high guluronate alginate was added to the islet suspension giving a final concentration of 3,000 rat islets per ml of 0.7% alginate in saline with 10 mM HEPES and 6 mM citrate.

EXAMPLE 4

Preparation of Coated Dog Pancreatic Islets

This example illustrates preparation of coated dog pancreatic islets used for transplantation in diabetic dog.

Approximately two hundred thousand dog islets prepared by the procedure of Example 3 were suspended in 2.5 ml 0.9% high guluronate alginate and transferred to a 3 ml plastic syringe by using a 16 g 2¼ inch i.v. catheter (Jelco 4062) with the needle removed. The catheter was then replaced with a 20 g blunt needle.

Using a DC electrostatic voltage of 8 KV (provided by a van de Graaff generator) between needle tip and grounded 117 mM aqueous calcium chloride solution at ambient temperature, a suspension of pancreatic islets (14 dog islets per μl) prepared by the procedure of Examples 1–3 was passed through a 20 gauge needle at a flow rate of approximately 200 μl/min. The suspension emerged from the needle as a thin, attenuated stream which transformed into droplets, the droplets being collected in a 60 mM petri dish (Flacon 1007) containing 10 ml calcium chloride solution (117 mM). The droplets were gelled by reaction with the calcium ions in the solution. The calcium alginate coatings on the islets were smooth and uniform and had an approximate thickness of about 130 μm. The total coated particles had an average diameter of about 360 μm.

This process was repeated with a suspension of 14 rat islets/μl prepared by the procedure of Example 3.

EXAMPLE 5

Process for Preparation of Multiple Coated Pancreatic Islets Transplants with Calcium Alginate This example illustrates the process for preparation of multiple coated dog pancreatic islets transplants using an extension of the calcium alginate crosslinking.

The islets were prepared according to Example 3 and coated according to Example 4. The single coated islets in spheres were divided into two samples of 1 ml spheres per 50 ml centrifuge tube (Corning 25339-50) in the calcium chloride collecting solution. Both samples separately were placed into 2.5 ml of 0.005% polylysine polymer having MW 200,000 dissolved in calcium chloride (120 mM) solution and left to react for 4 minutes. The islets were removed from the polymer solution and rinsed. The concentration of the calcium chloride was reduced from 120 mM to 24 mM by adding 40 ml sucrose water to 10 ml of calcium chloride solution containing the 1 ml spheres. After room temperature gravity sedimentation, all fluid was removed from the spheres. To one ml of spheres, 1.5 ml sucrose water was added quickly followed by 8 ml 4% high mannuronate alginate solution (Example 2) while vortexing. The mixture was rotated in the mixing tube for about 2 minutes. The outer coat was formed by using a spinning disc droplet generator, collecting the spheres in about 100 ml calcium chloride solution.

The spheres were gravity sedimented in three 50 ml centrifuge tubes. Each supernatant was reduced to 15 ml so that all three could be combined into one 50 ml tube. After another gravity sedimentation, the supernatant was reduced to 15 ml, including 7.5 ml spheres, and 35 ml saline added for a dilution of 1:3. After sedimentation, the process was repeated, making a 1:10 dilution by adding 40 mls of saline to 10 mls of the solution containing the spheres. The final calcium concentration was 4–6 mM.

EXAMPLE 6

Process for Preparation of Multiple Coated Pancreatic Islet Transplants with Barium Crosslinked Alginate This example illustrates the process for preparation of multiple coated pancreatic islet transplants with barium crosslinked alginate "halo".

The islets were prepared according to Example 3 and coated according to Example 4.

Excess calcium was removed from 1 ml spheres containing the islets by gravity sedimentation, removal of the supernatant, and resuspension in 15 ml sucrose water three times. Samples were placed into 0.005% polylysine polymer having MW 200,000 dissolved in 120 mM calcium chloride and left to react for 5 minutes. The polymer solution was removed and spheres were rinsed with a solution of two ml 100 ml barium chloride with 10 mM HEPES, added to 10 ml sucrose water. The spheres were let to reach a final concentration of 14 mM barium chloride. The sample was rotated for 5 minutes at room temperature. Excess barium was removed by washing 3 times with sucrose water as above. The supernatant was reduced to 1 ml and 3 ml. High mannuronate alginate (4%) (Example 3) was vortexed into the sample. The outer coat was formed by using a spinning disc droplet generator, collecting the spheres in calcium chloride solution. The calcium chloride was diluted to 4–6 mM by washing with saline as in Example 5.

EXAMPLE 7

Process for Preparation of Multiple Coated Pancreatic Islets Transplants with Strontium Crosslinked Alginate This example illustrates the process for preparation of multiple coated pancreatic islets transplants with strontium crosslinked alginate.

The islets were prepared according to Example 3 and with primary layer coated according to Example 4.

Soluble calcium was removed from 0.5 ml spheres containing islets by gravity sedimentation, removal of the supernatant, and by resuspension in 15 ml sucrose water. This process was repeated three times. Samples were placed into calcium chloride solution of 0.005% polylysine polymer having MW 200,000 and left to react for 3 minutes. Spheres were removed from the polylysine and rinsed with saline. Two ml 120 mM strontium chloride with 10 mM HEPES was added to 8 ml sucrose water containing the spheres to reach a final concentration of strontium 24 mM. The sample was rotated for 15 minutes at room temperature. Excess strontium was removed by washing three times with sucrose water as above.

All fluid was removed from the 0.5 ml spheres to which was added 1 ml sugar water and 2 ml of 4% high mannuronate alginate (Example 2) with gentle mixing. The outer coat was formed by using the air-knife, collecting the spheres in 10 ml calcium chloride solution. The calcium chloride was then diluted to 4–6 mM by washing with saline as in Example 5.

EXAMPLE 8

Transplantation of Pancreatic Islets Coated with Multiple Coating into Diabetic Mice This example illustrates the procedure used for testing the efficacy of the coated pancreatic islets in producing and delivering insulin in diabetic mice.

Host BALB/c mice were rendered diabetic by an IP injection of streptozotocin (250 mg streptozocin/kg body weight) in 0.1M citrate buffer, pH 4.5 several days prior to transplant Coated islets prepared by the procedure of Example 5 were injected into mice using a 16 g needle and a 3 ml syringe. Each animal received 0.2–2.0 ml spheres containing 500–2000 islets. Nine animals receiving multiple coated dog islets remained euglycemic from 54 days to 180 days. Three animals receiving double coated rat islets remained euglycemic for more than 300 days.

Empty alginate spheres coated with multilayer coating were prepared at the same time and injected IP into three diabetic mice. Blood glucose levels remained at 350–500 mg/dL. Both experimental diabetic and control mice were sacrificed at 30-day intervals and the coated spheres examined and found to be free from fibrosis or overgrowth by macrophages.

EXAMPLE 9

Transplantation of Pancreatic Islets Coated with Multiple Coating into Diabetic Dog This example illustrates the procedure used for testing the efficacy of the coated pancreatic islets in producing and delivering insulin in diabetic dogs.

A dog was made diabetic by total pancreatectomy. Following surgery its blood glucose level was elevated to 242 mg/dL and it required 5–7 U of NPH insulin to keep it below 250 mg/dL. The animal was transplanted while under a general anesthesia. A 14 gauge angiocatheter was inserted midline into the peritoneal cavity of the dog. After removing the needle, the multiple coated islets were injected through the catheter from a 60 ml syringe. Each syringe contained 10 ml spheres in 50 ml Dulbecco's Medium. The dog was injected with 94,000 multilayer coated islets 8 days post pancreatectomy, with 154,000 coated islets 3 days later, and 150,000 coated islets 6 days after that for a total of about 400,000 islets. There were an average of about 2,300–2,600 islets/ml spheres. After transplantation, the dog's blood glucose levels were monitored several times each day. The dog was maintained on an average of 4.5 U insulin/day for two weeks post transplant. The insulin was reduced 0.5 U every two days for the next 20 days and then removed entirely from insulin therapy. The dog has remained euglycemic for 90 days and up to date.

EXAMPLE 10

Multilayer Coating of Calcitonin Secreting Cells

This example illustrates a multiple layer coating of calcitonin secreting cells.

A suspension of a calcitonin secreting cell line, MXH-5, ($2.5 \times 10^6$) were coated with multilayer coating alginate according to Examples 1–6. The second coating was applied according to Example 6, using an air knife. Barium chloride was used as a gelling solution.

After the polymer barrier is emplaced and the gel gradient generated, coated capsules were tested for viability, and cell functionality by using trypan blue dry exclusion and by alamar Blue assay.

More than 68% of the coated calcitonin secreting cells had size within 30–200 $\mu$m. More than 60% of the coated cells were viable and functional. They were able to secrete over 200 pg/ml of calcitonin which corresponds to over 50% of the amount secreted by neat uncoated cells in culture.

Other secretory cells maintained in a suitable cell culture were coated in a similar manner.

EXAMPLE 11

Multiple Coating of Hepatocytes

This example illustrates coating of isolated hepatocytes.

Hepatocytes are isolated in a manner similar to the isolation of pancreatic cells described in Example 3. Cells are then coated according to any one procedure described in Examples 1–7.

After the multilayer coating is applied, the size of the coated cells is determined and the viability and functionality of the coated cells for hepatic replacement are tested.

What is claimed is:

1. A method for preparation of multilayer coating of a biological tissue core comprising the steps:
    (a) suspending the core in a solution of a first alginate to form a first suspension solution;
    (b) dispersing the suspension of step (a);
    (c) gelling the first alginate with a solution of divalent cations;
    (d) transferring the gelled spheres of step (c) into about 0.005% to about 0.0005% polyamino acid polymer solution, said polymer having molecular weight from about 10,000 to about 450,000 for about 0.5 to about 5 minutes;
    (e) suspending the spheres of step (d) in a second alginate solution;
    (f) dispersing the spheres of step (e); and
    (g) gelling the second alginate in a second divalent cation solution.

2. The method of claim 1 wherein the first alginate is guluronate-rich alginate.

3. The method of claim 2 wherein the second alginate is mannuronate-rich alginate.

4. The method of claim 2 wherein the divalent cation in step (c) is selected from the group consisting of barium, strontium or calcium.

5. The method of claim 4 wherein the different divalent cation is calcium and the solution of divalent cations is calcium chloride.

6. The method of claim 1 wherein the spheres of step (c) are dispersed by an air knife, spin encapsulation apparatus or electrostatic droplet generator.

7. The method of claim 2 wherein the primary layers of coating are formed by suspension of the core in the first alginate.

8. The method of claim 7 wherein in step (d) polyamino acid polymer is selected from group consisting of polylysine, polyornithine or polyarginine polymer.

9. The method of claim 8 wherein the polyamino acid polymer is polylysine polymer.

10. The method of claim 2 wherein a molecular weight of the first alginate is from about 80 to about 300 kilodaltons and wherein the alginate is guluronate-rich alginate.

11. The method of claim 3 wherein a molecular weight of the second alginate is from about 40 to about 120 kilodaltons and wherein alginate is mannuronate-rich alginate.

12. The method of claim 1 wherein the coat comprises a primary layer, a polyamino acid barrier, a secondary layer and a tertiary layer.

13. The method of claim 12 wherein the primary layer is a gelled alginate, wherein the barrier is made of a polylysine polymer, wherein the secondary layer is soft gel "halo" and wherein the tertiary layer is gelled alginate.

14. The method of claim 5 wherein the total thickness of the coating ranges from 20 to 200 $\mu$m.

15. A transplant suitable for transplantation into a host containing a core of viable, functional and physiologically active biological tissue, cells or cell lines coated with a multiple alginate coat comprising a primary layer of gelled alginate, polyamino acid polymer barrier, secondary "halo" layer formed by ionic exchange and partial displacement of calcium ions with sodium ions generating gel gradient, and a tertiary layer of sodium alginate gelled with divalent cations.

16. The transplant of claim 14 wherein the multilayer alginate coating has the total thickness from about 20 to about 200 $\mu$m.

17. The transplant of claim 14 wherein the multilayer alginate coating conforms to the surface of the core and forms an insoluble immunological barrier.

18. The transplant of claim 17 wherein said core is an allograft, xerograph, pancreatic islet, endocrine gland tissue, a primary cell or cell line.

19. The transplant of claim 17 wherein the core is a pancreatic islet cell.

* * * * *